(12) United States Patent
Khamar et al.

(10) Patent No.: US 9,795,659 B2
(45) Date of Patent: Oct. 24, 2017

(54) PHARMACEUTICAL COMPOSITION OF KILLED CELLS WITH SUBSTANTIALLY RETAINED IMMUNOGENICITY

(75) Inventors: Bakulesh Mafatlal Khamar, Ahmedabad (IN); Satinder Singh, Ahmedabad (IN); Nirav Manojkumar Desai, Ahmedabad (IN); Rajiv Indravadan Modi, Ahmedabad (IN)

(73) Assignee: Cadila Pharmaceuticals, Ltd. (IN)

( * ) Notice: Subject to any disclaimer, the term of this patent is extended or adjusted under 35 U.S.C. 154(b) by 154 days.

(21) Appl. No.: 13/579,607

(22) PCT Filed: Feb. 17, 2011

(86) PCT No.: PCT/IB2011/050655
§ 371 (c)(1),
(2), (4) Date: Aug. 17, 2012

(87) PCT Pub. No.: WO2011/101796
PCT Pub. Date: Aug. 25, 2011

(65) Prior Publication Data
US 2012/0308605 A1    Dec. 6, 2012

(30) Foreign Application Priority Data

Feb. 19, 2010 (IN) .......................... 464/MUM/2010

(51) Int. Cl.
*A61K 35/13*   (2015.01)
*A61K 39/00*   (2006.01)
*A01N 1/00*    (2006.01)

(52) U.S. Cl.
CPC ............ *A61K 39/0011* (2013.01); *A01N 1/00* (2013.01); *A61K 35/13* (2013.01); *A61K 2039/5152* (2013.01)

(58) Field of Classification Search
None
See application file for complete search history.

(56) References Cited

U.S. PATENT DOCUMENTS 5,648,206 A  *  7/1997  Goodrich et al. ................ 435/2
8,048,434 B2 * 11/2011  Khamar et al. ............ 424/248.1

OTHER PUBLICATIONS

International Search Report and Written Opinion issued by the PCT on Jun. 24, 2011.

\* cited by examiner

*Primary Examiner* — Yunsoo Kim
(74) *Attorney, Agent, or Firm* — Burns & Levinson, LLP (57) ABSTRACT

This invention discloses the process for lyophilization of the treated cells which comprises the use of a solution containing Trehalose along with amphipathic polymer Polyvinylpyrrolidone. Further the invention discloses the process treating cancer cells, freezing, lyophilizing and reconstituting. Immunomodulator treated dead, but intact cancerous cells were recovered, which can subsequently be used for cancer immunotherapy.

4 Claims, 7 Drawing Sheets

PHARMACEUTICAL COMPOSITION OF KILLED CELLS WITH SUBSTANTIALLY RETAINED IMMUNOGENICITY

CROSS REFERENCE TO RELATED APPLICATION

This is a §371 U.S. National Stage of PCT Application No. PCT/IB2011/050655, filed Feb. 17, 2011, which was published in English under PCT Article 21(2), which in turn claims the benefit of and priority to the Indian Application No. 464/MUM/2010, filed on Feb. 19, 2010, which is incorporated by reference herein in its entirety.

FIELD OF INVENTION

The current invention unveils a pharmaceutical composition of killed whole cells with substantially retained immunogenicity and methods of preparing there of.

BACKGROUND OF INVENTION

Vaccine preparation from single antigen or biomarker has limited immunogenicity to provide desired/required protective immunity. To achieve broad spectrum protection a combination/repertoire of antigens is required. Such a combination is possible by the use of whole cells as they comprises of different immunogenic markers and antigens.

Cancer cells if used live as vaccine can cause cancerous growth and can imbibe disease. The use of killed cells has been restricted due to their limited stability. There is persistent demand to stabilize dead cells whilst retaining their immunological and structural properties. Though several efforts to preserve live cells are well documented, to our knowledge there are no reports available on dead cell preservation with retention of their immunological properties for immunization purpose.

Whole cells when used as vaccine generate better immune response when compared to cells lysates which is attributed to the repertoire of immunogenic epitopes, characterized or uncharacterized, on cell surface.

Hardev S. Pandha, Dorthe Cook, Rebecca Greenhalgh and Angus Dalgleish described use of killed cells (2005 BJU INTERNATIONAL, 95, 1336-1343) for Immunotherapy of murine prostate cancer. The immunogenicity of irradiated tumour cells is enhanced when they are killed ex-vivo using suicide-gene therapy.

Adjuvant is an agent that may stimulate the immune system and increase the response to a vaccine, without having any specific antigenic effect in itself (NCI, Definition). The word "adjuvant" comes from the Latin word adiuvare, meaning to help or aid. "An immunologic adjuvant is defined as any substance that acts to accelerate, prolong, or enhance antigen-specific immune responses when used in combination with specific vaccine antigens" (*DNA Vaccines: Methods and Protocols*, D. B. Lowrie and R. G. Whalen, Humana Press, 2000).

There are many known adjuvants in widespread use, including oils, aluminium salts, and virosomes, live or dead whole organisms, and extracts of microbes. The use of these adjuvants is also recommended in cancer vaccines to augment the immune stimulation by antigen/s.

U.S. Pat. No. 5,059,518 discloses the method of preservation of live Hybridoma cell lines, tissue cells and control cells for immunoassays and hematological measurements. The method comprises of isolation of Peripheral blood lymphocytes, resuspending cell pellet in phosphate buffered albumin and treating cells with isotonic solution of Intracellular cryopreservative Trehalose followed by lyophilisation. The lyophilates were resuspended in isotonic trehalose solution. Fluorescent Antibody labeled Cell Sorter (FACS) was used to characterize the antigenic determinants in Control and lyophilized cell population U.S. Pat. No. 5,045,446 discloses preservation of live RBCs while retaining their metabolic activity. The patent discloses the use of intracellular cryopreservatives such as Galactose/Mannose/Xylose/Fructose/Glucose at concentration from (12.2-21.7%) along with extracellular PVP (of Mol. Wt. 10K-24K). The samples were rehydrated at 37° C. using 25.5% sucrose solution in Phosphate buffered Saline. Intact cell recovery was 52.9+7.9% after incorporating the polymer with carbohydrate Galactose, Mannose, Xylose, Fructose, Glucose, Trehalose and sucrose in lyophilisation solution showed marginal cell recovery. Carbohydrate (sucrose, trehalose, mannose, glucose in order of preference) was used at a concentration of 3.6% in reconstitution medium.

U.S. Pat. No. 5,648,206 reveals preservation of live RBCs with retained metabolic activity. The patent discloses the use of intracellular cryopreservative such as Galactose/Mannose/Xylose/Fructose/Glucose at concentration from (12.2-21.7%) with extracellular cryoprotactant PVP of Mol. Wt. 10K-24K. Lyophilisation medium contained monosaccharide (Xylose, glucose, mannose, ribose, fructose) at a concentration from 7%-37.5%. Extracellular cryoprotactant (PVP/Dextran) having a molecular weight from about 1K to 360K used at concentration of about 0.7%. The data of Trehalose combined with PVP is not disclosed though the patent claims that when trehalose and PVP were used together in lyophilzation solution they showed marginal cell recovery.

U.S. Pat. No. 5,425,951 discloses preservation of live RBCs retaining their metabolic activity. The patent describes the method of reconstituting lyophilized cells comprising the steps of treating cells with an aqueous solution containing a carbohydrate (Glucose/mannose; trehalose/sucrose) at a concentration of at least 1% and a polymer having a molecular weight of from IK to about 360K (PVP) at a concentration of about 20% by weight.

US Patent Application number 2005/0084481 A1 discloses preservation of mammalian and vertebrate cells, for example Macrophages and hematopoietic stem cells expressing P2X7 receptor.

European Patent EP0444159B1 discloses preservation of mammalian cells, hybridoma cell lines, tissue cells for immunoassays and other hematological measurements. Isotonic fluid containing 10% Trehalose was used for preserving proteinaceous markers on surface of mammalian cells. The steps involved resuspending the mammalian cells in phosphate buffered albumin and incubating the resultant pellet obtained after centrifugation in isotonic solution of 10% Trehalose at ambient temperature for approx. 30 min. This was followed by slow chilling at about −70° C. for approx. an hour.

During the slow freezing process, the extra cellular water will freeze first and salts will be left out, which will damage the cell membrane of dead cells. In case of live cells (eg. During cell culture) slow freezing is recommended (Biochimica et Biophysica Acta (BBA)—Biomembranes. Volume 1768, Issue 3, March 2007, Pages 728-736)

PCT publication WO97/04801 (PCT/US96/12251) discloses the use of sucrose and trehalose as cryo-preservatives. The invention encompasses anti-HER2 antibody. Histidine/Succinate buffer based pre-lyophilized formulation was developed to maintain pH of formulation. Polysorbate was added in pre-lyophilized formulation to reduce aggregation of reconstituted protein and formation of particulates. The patent also discloses the use of aromatic alcohols such as benzyl or phenol alcohol in reconstituting diluents. Trehalose based lyopreservative buffer was found to aid in stabilization of protein for 2 weeks at 40° C. and increase in trehalose concentration increased the stability for 1 year at 30° C. Addition of trehalose and sucrose also prevented aggregation at above said storage condition.

U.S. Pat. No. 5,759,774 discloses method of detecting circulating antibody types using dried or lyophilized cells. The patent discloses the preservation of mammalian cells notably RBCs, lymphocytes, platelets lipoosomes and hemosomes. Inventors used carbohydrate-polymer solution as lyophilisation preservative wherein the carbohydrate could be xylose mannose, glucose, ribose, mannose or fructose and Polymer could be PVP, HES or Dextran. The concentrations of monosaccharide pentoses and hexoses ranged from 7-37.5%. They also modified lyophilisation buffer composition through addition of glutathione inosine, adenine nicotinic acid glutamine, $MgCl_2.6H_2O$, Dextrose, PVP and HES and reconstitution buffer constituents by adding ATP, $KH_2PO_4$, $Na_2HPO_4$ and PVP.

European Patent EP 90906036 discloses method of lyophilisation of mammalian peripheral blood cells, cultured cells, hybridoma cell lines or tissue cells. The steps comprised of incubating the cell pellet, after centrifugation, in isotonic Trehalose solution followed by subjecting the cell suspension to freezing at −70° C. before lyophilisation. The lyophilized cells were reconstituted in distilled water.

PCT publication WO92/14359 (PCT/US92/00782) describes the method of lyophilisation of mammalian sperm cells. The patent discloses use of monosaccharide, preferably glucose in the concentration of about 0.1-2.6 M and polymer (or a mixture of polymers) with molecular weight preferably in the range of 1K to 350k. The preferred polymer was PVP followed by Dextran, HES and Poloxamers. PBS was used as lyophilisation buffer with pH in range of about 7.0 to 7.4. Suggested reconstituted medium comprised of Polymer (MW 15K) and PBS containing glucose and adenine. Typical cell metabolites such as ATP and NAD were incorporated along with monosaccharide such as xylose, glucose, ribose, mannose and fructose (at a concentration of 1M) in addition to glucose.

US Patent application 20080057040 discloses cryopreservation of stem cells. U.S. Pat. No. 5,071,741 discloses use of Agarose and alginate as non permeating and Glycerol and DMSO (at concentration of 1M) as permeating, in cryopreservation of cellular matter (bovine aortic endothelium derived cell line-BFA-Clone 1 & Islets of Langerhans from Murine Pancreas).

U.S. Pat. No. 4,004,975 discloses the Method of Isolating and Cryopreserving, at −80° C., Human White Cells from Whole Blood. The patent suggests combination of intracellular cryopreservative (5% DMSO) & extracellular cryopreservative (4% HES).

PCT publication WO 92/14360 (PCTUS92/00650) describes the method of lyophilisation and reconstitution of mixture of nucleated Non-Mammalian cells and blood matter. The method was invented with the aim of developing vaccines against *Anaplasrna Marginal* (Toxoplasma), The process streamlines continuous supply of blood samples infected with *Analplasma* spp (centrale) as the sample lyophilates can be stored for extended period of time. The lyophilisation mixture comprised of Monosaccharide (hexose and pentose) with at least two biocompatible amphipathic polymers. The monosaccharide was selected from the group consisting of Xylose, Glucose, Ribose, Mannose and fructose. The reconstitution buffer contained polymer at final concentration 0.7%.

The live cell membrane tonicity is maintained and we need some membrane pore opening agents/ATP to open up the pores for internalization of intracellular cryopreservant to replace water of hydration for preservation or cryopreservation (US2005/0084481 A1).

During live cell preservation it is also desirable to provide some carbon/ATP source (eg. Adenine) to keep them metabolically active (Advances in Biopreservation by John G. Baust) conversely it is also desirable to maintain adequate moisture content to keep them minimally metabolically active so that they can be revived later (US Patent Application 20100297231).

In case of live cell preservation there are chances of surface protein variability as a consequence of response to changing microenvironment due to addition of cryopreservants. However, dead cells may respond minimally (or not at all) to changing microenvironment conditions, because of defective/impaired protein synthesis machinery (Annual Review of Biophysics and Bioengineering. Vol. 3: 341-363).

It is desirable to preserve the integrity and immunogenicity of killed cells. The preservation of morphology and intactness of killed cells is useful for various purposes including developing immune mechanism associated therapies (Infect Immun. 1978 July; 21(1): 348) and diagnostics (Diagnostic Microbiology and Infectious Disease Volume 62, Issue 2, October 2008, Pages 133-141).

The direct influence of the osmotic stress on the cell membrane is documented for dead cells with observation of endocytotic vesiculation; membrane fluidity changes and increased membrane phase transition temperature. This Membrane phase transition which is believed to initiate lipid phase separation and membrane fusion may directly affect the viability of dehydrated dead cells. Also due to coexistence of the different phases during a phase transition, membrane permeability increases and cells may become leaky cellular contents during re-hydration will lead to reduction in intact cells number.

The method known for the preservation of live cells cannot be extended to preserving killed cells as
1. Dead cells loose membrane tonicity/plasticity and thus may collapse during freeze drying.
2. Dead cells forms aggregates which can be partially attributed to the presence of extracellular DNA of damaged dead cells.
3. The membrane integrity of internal organelles of dead cells is compromised and thus it is really challenging to maintain internal cellular architecture. (Morphological Features of Cell Death. News in Physiological Sciences, (2004) Vol. 19, No. 3, 124-128.)
4. Dead cells have different endocytotic vesiculation: membrane fluidity changes and membrane phase transition temperatures.
5. Dead cells respond minimally (or not at all) to changing microenvironment conditions, because of defective/impaired protein synthesis machinery.

Morphology of a cell as defined herein relates to the size, shape and structure of cell.

The present invention relates to a method of preserving killed cells. The method involves lyophilisation followed by reconstitution wherein the morphology, integrity and immunogenicity of the cells are retained even on prolonged storage. Further, pharmaceutical compositions comprising the killed cell retaining immunogenicity are disclosed. Such compositions find applications as Vaccines. The composition optionally contains one or more adjuvant to enhance the immunogenicity of the killed cells.

DESCRIPTION OF DRAWINGS

FIGS. 2 A & B: Determination of Cellular Integrity using a cell membrane lyophilic stain PKH126 dye.

FIG. 4: Cells with intact cell membrane and Nuclear Envelope

FIG. 5: Immunogenicity of lyophilized and then reconstituted cells

FIG. 6: Surface marker staining under fluorescence microscope

DESCRIPTION OF THE INVENTION

Surprisingly it has been found that a stable composition of killed cells with substantially retained immunogenic properties can be prepared comprising of killed cells, at least one intracellular cryo preservative at least one extra cellular cryo preservative and excipients.

The intracellular cryo preservative is selected from carbohydrates such as monosaccharides and diasaccharides. Surprisingly it has been found that trehalose as intracellular cryo preservative for maximizing intact cell recovery yields highest cell recovery. The carbohydrate as an intracellular cryo preservative used is between 1 to 10% W/V concentration.

The extra cellular cryo preservative is selected from amphipathic substances such as Hydroxyethylstarch (HES), Dextran and Polyvinylpyrrolidone (PVP) and ploysorbates.

Surprisingly the amphiphathic polymer Polyvinylpyrrolidone (PVP) has been found to be improving intact cell recovery as extra cellular cryo preservative. The PVP used as an extra cellular cryo preservative is between 0.1 to 5% W/V concentration. The molecular weight of PVP used is in the range 30 to 50 kilo Daltons.

Surprisingly the amphiphathic polymer Hydroxyethylstarch (HES) has been found to be improving intact cell recovery as extra cellular cryo preservative. The HES used as an extra cellular cryo preservative is between 0.1 to 5% W/V concentration. The molecular weight of HES used is in the range 30 to 50 kilo Daltons.

Surprisingly the amphiphathic polymer Dextran has been found to be improving intact cell recovery as extra cellular cryo preservative. The dextran used as an extra cellular cryo preservative is between 0.1 to 5% W/V concentration. The molecular weight of dextran used is preferably in the range of 30 to 50 kilo Daltons.

Surprisingly the amphiphathic polymer polysorbate has been found to be improving intact cell recovery as extra cellular cryo preservative. The polysorbate used as an extra cellular cryo preservative is between 0.1 to 5% W/V concentration. The amphiphathic polymer polysorbate used as extra cellular cryo preservative is selected from Polysorbate 20, Polysorbate 40, Polysorbate 60, Polysorbate 65, Polysorbate 80 preferably Polysorbate 80

In accordance with the Invention the process of preparing a stable composition of killed cells with substantially retained immunogenic properties is in following steps 1. Treating killed cells with Intracellular cryo-preservatives.
2. Treating killed cells with Extracellular cryo-preservatives.
3. Snap chilling in to frozen formulation prior to lyophilisation.
4. Lyophilisation of treated killed cells.
5. Reconstitution of lyophilates (of killed cells).
6. Assessing preservation of cellular integrity.
7. Assessing effectiveness of preservation method.
8. Evaluating preservation of antigenic/immunogenic properties.

The lyophilisation solution buffered at pH of 7.4 by Dulbecco's Phosphate Buffered Saline (DPBS—without Calcium Chloride and Magnesium Chloride), the Components of which were Potassium Phosphate Monobasic (0.20 g/L); Potassium Chloride (0.20 g/L); Sodium Chloride (8.00 g/L) and Anhydrous Sodium Phosphate Dibasic (1.15 g/L). The lyophilisation buffer contains a final concentration of about 5% weight by volume of a non reducing disaccharide, preferably Trehalose and a final concentration of about 1% weight by volume of a polymer, preferably Polyvinylpyrrolidone (Mol. Weight. 44K).

The morphological preservation, integrity and retention of immunogenicity even on prolonged storage of killed cell composition were analyzed as follows 1. Morphological profiling (Size):—Flow Cytometry. PKH26 for integrity of ell membrane. Hematoxylin and Eosin staining for cytoplasmic and nuclear membrane integrity
2. Physiochemical Profiling:—Confirming Cell death uses TOPRO3 Iodide Dye.
3. Granularity assay:—FACS FSC/SSC
4. Cytogenetic analysis
5. DNA Profiling: FACS DNA content Analysis.
6. DNA Extraction and agarose gel electrophoresis to assess DNA integrity
7. Immunophenotyping:—HLADR molecules
8. Immunological Profiling:—$CD4^+$. Cytotoxic evaluation of $CD8^+$ and NK Cells with cyto-toxic determinants: Perforin and Granzyme.
9. Functional Assay:—FACS Effector Function Assay using PKH26 and TOPRO3 iodide to identify/confirm and enumerate dead Target cells. Quantification of IFNγ and IL-2 producing splenocytes. Lymphocyte Proliferation assay Using PKH 26.

Example 1: Extracellular Cryopreservative $10^7$ cells/ml of cancer cells were treated with *Mycobacterium w* (Mw). Percentage cell death was determined employing Trypan blue dye exclusion principle. Cells were pelleted by centrifugation at 1500 rpm for 10 min. The Supernatant was discarded and control Pellet was resuspended in DPBS. The total volume was distributed into aliquots of 1 ml each and cells in each aliquot were counted. Treatment group pellet was re-suspended in Lyophilisation buffer solution containing 1% PVP w/v. Each aliquot was subjected to snap chilling in Liquid nitrogen (below −100° C.) followed by lyophilisation. Treatment group percent intact cell recovery, estimated after reconstitution of lyophiliates, was 19.125±3.275

Example 2: Intracellular Cryopreservative $10^7$ cells/ml of cancer cells were taken and treated with Mw. Percentage cell death was determined employing Trypan blue dye exclusion principle. Cells were pelleted by centrifugation at 1500 rpm for 10 min. Supernatant was discarded and control group cell pellet was resuspended in DPBS. Total volume was distributed into aliquots of 1 ml each and cells in each aliquot were counted. Treatment group cell pellet was resuspended in Lyophilisation buffer solution containing 5% Trehalose w/v. Each aliquot was subjected to snap chilling in Liquid nitrogen (below −100° C.) followed by lyophilisation. Treatment group percent intact cell recovery upon reconstitution of lyophilate in DPBS, estimated using hemocytometer, was 15.27±0.64.

Example 3: Surfactant Polymers for Cryopreservative Activity $10^7$ cells/ml of cancer cells were taken and treated with Mw. Percent cell viability was determined using trypan blue exclusion assay. Cells were pelleted by centrifugation at 1500 rpm for 10 min. Supernatant was discarded and control group cell pellet resuspended in DPBS. Total volume was distributed into aliquots of 1 ml each and cells in each aliquot were counted. Treatment group cell pellet was resuspended in Lyophilisation buffer containing 0.05% Polysorbate 80 v/v. Each aliquot was subjected to snap chilling in Liquid nitrogen (below −100° C.) followed by lyophilisation. Treatment group percent intact cell recovery upon reconstitution of lyophilate in DPBS, estimated using hemocytometer, was about 0.9.

Example 4: Extracellular Cryopreservative Treatment Followed by Intracellular Cryopreservative Treatment $10^7$ cells/ml of cancer cells were treated with Mw. Percentage cell death was determined employing Trypan blue dye exclusion principle. Cells were pelleted by centrifugation at 1500 rpm for 10 min. Supernatant was discarded and control group cell pellet resuspended in DPBS. Total volume was distributed into aliquots of 1 ml each and cells in each aliquot were counted. Treatment group cell pellet was resuspended in PVP at final concentration of 1% w/v (in DPBS). Cell suspension was incubated at 37° C. for 15 min. subsequently, trehalose was added at final concentration of 5% w/v (in DPBS) followed by incubation at 37° C. for 15 min. Total volume was distributed into aliquots of 1 ml each and cells in each aliquot were counted. Prior to lyophilisation, each aliquot was subjected to snap chilling in Liquid nitrogen (below −100° C.). Treatment group Percent intact cell recovery, upon reconstitution of lyophilate in DPBS was 28.08±3.63

Example 5: Intracellular Cryopreservative Treatment Followed by Extracellular Cryopreservative Treatment $10^7$ cells/ml of cancer cells were treated with Mw. Percent cell viability was determined using trypan blue exclusion assay. Cells were pelleted by centrifugation at 1500 rpm for 10 min. Supernatant was discarded and control cell pellet resuspended in DPBS. Total volume was distributed into aliquots of 1 ml each and cells in each aliquot were counted. Treatment group cell pellet was resuspended in trehalose at final concentration of 5% w/v (in DPBS) followed by incubation at 37° C. for 15 min. Subsequently PVP was added at final concentration of 1% w/v and cell suspension was incubated at 37° C. for 15 min. Total volume was distributed into aliquots of 1 ml each and cells in each aliquot were counted. Prior to lyophilisation, all aliquots were subjected to snap chilling in Liquid nitrogen (below −100° C.). Treatment group percent intact cell recovery was 55.61±4.35.

Example 6: Intracellular Cryopreservative Followed by Extracellular Cryopreservative $10^7$ cells/ml of cancer cells were treated with Mw. Percentage cell death was determined employing Trypan blue dye exclusion principle. Cells were pelleted by centrifugation at 1500 rpm for 10 min. Supernatant was discarded and control group cell pellet resuspended in DPBS. Total volume was distributed into aliquots of 1 ml each and cells in each aliquot were counted. Treatment group cell pellet was resuspended in dextrose at final concentration of 5% w/v (in DPBS) followed by incubation at 37° C. for 15 min. Subsequently HES was added at final concentration of 1% w/v and cell suspension was incubated at 37° C. for 15 min. Total volume was distributed into aliquots of 1 ml each and cells in each aliquot were counted. Prior to lyophilisation, all aliquots were subjected to snap chilling in Liquid nitrogen (below −100° C.). Post lyophilisation, treatment group percent intact cell recovery was ~54.88, but cellular morphology was disturbed.

Example 7: Intracellular Cryopreservative Followed by Extracellular Cryopreservative $10^7$ cells/ml of cancer cells were treated with Mw. Percent cell viability was determined using trypan blue exclusion assay. Cells were pelleted by centrifugation at 1500 rpm for 10 min. Supernatant was discarded and control group cell pellet was resuspended in DPBS. Total volume was distributed into aliquots of 1 ml each and cells in each aliquot were counted. Treatment group cell pellet was resuspended in Glycerol at final concentration of 5% v/v (in DPBS) followed by incubation for 15 min. at 37° C. Subsequently HES was added at final concentration of 1% w/v and cell suspension was incubated at 37° C. for 15 min. Total volume was distributed into aliquots of 1 ml each and cells in each aliquot were counted prior to lyophilisation. All aliquots were subjected to snap chilling in Liquid nitrogen (below −100° C.). Post lyophilisation, treatment group percent intact cell recovery was ~46.19, albeit cellular morphology was disturbed.

Example 8: Intracellular Cryopreservative Followed by Extracellular Cryopreservative $10^7$ cells/ml of cancer cells were treated with Mw. Percentage cell death was determined employing Trypan blue dye exclusion principle. Cells were pelleted by centrifugation at 1500 rpm for 10 min. Supernatant was discarded and control group cell pellet was resuspended in DPBS. Total volume was distributed into aliquots of 1 ml each and cells in each aliquot were counted. Treatment group cell pellet was resuspended in Sucrose at final concentration of 5% w/v (in DPBS) followed by incubation for 15 min. at 37° C. Subsequently HES was added at final concentration of 1% w/v and cell suspension was incubated at 37° C. for 15 min. Total volume was distributed into aliquots of 1 ml each and cells in each aliquot were counted prior to lyophilisation. All aliquots were subjected to snap chilling in Liquid nitrogen (below −100° C.). Post lyophilisation, treatment group percent intact cell recovery was ~47.25, but cellular morphology was disturbed.

Example 9: Extracellular Cryopreservative Followed by Intracellular Cryopreservative with Additives $10^7$ cells/ml of cancer cells were treated with Mw. Percent cell viability was determined using trypan blue exclusion assay. Cells were pelleted by centrifugation at 1500 rpm for 10 min. Supernatant was discarded and control group cell pellet was resuspended in DPBS. Total volume was distributed into aliquots of 1 ml each and cells in each aliquot were counted. Treatment group cell pellet was resuspended in PVP at final concentration of 1% w/v (in DPBS) followed by incubation for 15 min. at 37° C. Subsequently, trehalose at final concentration of 5% w/v was added, followed by additives (Nicotinic Acid 0.75 mM; Glutamine 0.75 mM; $MgCl_2$ 0.49 mM and Histidine 5 mM) at final concentration of 1%. Cell suspension was incubated at 37° C. for 15 min. Cells in each aliquot were counted prior to lyophilisation. All aliquots were subjected to snap chilling in Liquid nitrogen (below −100° C.). Post lyophilisation, treatment group percent intact cell recovery was ~11.0

Example 10: Intracellular Cryopreservative Followed by Extracellular Cryopreservative with Additives $10^7$ cells/ml of cancer cells were treated with Mw. Percentage cell death was determined employing Trypan blue dye exclusion principle. Cells were pelleted by centrifugation at 1500 rpm for 10 min. Supernatant was discarded and control group cell pellet was resuspended in DPBS. Total volume was distributed into aliquots of 1 ml each and cells in each aliquot were counted. Treatment group cell pellet was resuspended in Trehalose at final concentration of 5% w/v (in DPBS) followed by incubation for 15 min. at 37° C. Subsequently, PVP at final concentration of 1% w/v was added, followed by additives (Nicotinic Acid 0.75 mM; Glutamine 0.75 mM; $MgCl_2$ 0.49 mM and Histidine 5 mM) at final concentration of 1%. Cell suspension was incubated at 37° C. for 15 min. Cells in each aliquot were counted prior to lyophilisation. All aliquots were subjected to snap chilling in Liquid nitrogen. Post lyophilisation, treatment group percent intact cell recovery was ~48.9

Example 11: Freezing Method $1 \times 10^7$ cells/ml were treated with Mw. Percentage cell death, employing Trypan blue dye exclusion principle, was 60%. 5 aliquots were made and cells were pelleted down by centrifugation at 1500 rpm for 10 min. Of the 5 cell pellets obtained, 1 each resuspended in 100 µl of 50× Trehalose followed by incubation for 15 min. at 37° C. Final volume made upto 1 ml with DPBS. From each aliquot 200 µl distributed in glass vials labeled appropriately and cells in each aliquot were counted. All aliquots were subjected to slow freezing viz. at 8° C. for 1 hr, 4° C. for 2 hr, −20° C. for 4 hr and finally at −−70° C. for 8 hrs. Except for one freezing control, rest all aliquots subjected to lyophilisation for approx 48 hrs. Lyophilates reconstituted with 200 µl of DPBS and total no of intact cells counted using haemocytometer. Freezing control yielded 13% intact cells while lyophilisation resulted in 2% recovery.

Example 12: Freezing Method $1 \times 10^7$ cells/ml were treated with Mw. Percentage cell death, employing Trypan blue dye exclusion principle, was 60%. 5 aliquots were made and cells were pelleted down by centrifugation at 1500 rpm for 10 min. Of the 5 cell pellets obtained 1 each resuspended in 100 µl of 10× PVP followed by incubation for 15 min. at 37° C. Final volume made upto 1 ml with DPBS. From each aliquot 200 µl distributed in glass vials labeled appropriately and cells in each aliquot were counted. All aliquots were subjected to slow freezing viz. at 8° C. for 1 hr, 4° C. for 2 hr, −20° C. for 4 hr and finally at −70° C. for 8 hrs. Except for one freezing control, rest all aliquots subjected to lyophilisation for approx 48 hrs. Lyophiliates reconstituted with 200 µl of DPBS and total no of intact cells counted using haemocytometer. Freezing control yielded 32% intact cells while lyophilisation resulted in 5% recovery.

Example 13: Freezing Method $1 \times 10^7$ cells/ml were treated with Mw. Percentage cell death, employing Trypan blue dye exclusion principle was 60%. 5 aliquots were made and cells were pelleted down by centrifugation at 1500 rpm for 10 min. Of the 5 cell pellets obtained 1 each resuspended in 100 µl of 10× Dextran Sulfate followed by incubation for 15 min. at 37° C. Final volume made upto 1 ml with DPBS. From each aliquot 200 µl distributed in glass vials labeled appropriately and cells in each aliquot were counted. All aliquots were subjected to slow freezing viz. at 8° C. for 1 hr, 4° C. for 2 hr, −20° C. for 4 hr and finally at −70° C. for 8 hrs. Except for one freezing control, rest all aliquots subjected to lyophilisation for approx 48 hrs. lyophilized cell pellets reconstituted in 200 µl of DPBS and total no of intact cells counted using haemocytometer. Freezing control yielded 5% intact cells while no intact cell was observed after lyophilisation.

Though several intra-cellular and extra-cellular cryo-preservatives were capable of preserving the morphology and intactness of killed cells, trehalose and PVP appear advantageous over others.

Example 14

$1 \times 10^7$ B16F1 cells/ml treated with Mw. Percentage Cell death, employing Trypan blue dye exclusion principle was 25%. Cells were pelleted by centrifugation at 1500 rpm for 10 min. Supernatant was discarded. Cell pellets were resuspended in either 100 µl of 50× Trehalose or 100 µl 10× PVP and incubated at 37° C. for 15 min. Final volume was made upto 1 ml with DPBS. Five aliquots of 200 µl each were made and cells in each aliquot were counted prior to lyophilisation. Samples snap freezed in liquid nitrogen. Except one freezing control, rest all samples were subjected to lyophilisation for approx 48 hrs. Lyophilates reconstituted with 200 µl of DPBS and total no of intact cells counted using haemocytometer. Freezing control yielded 39% intact cells while lyophilisation resulted in 9% intact cell recovery. A combination of the two cryopreservatives appears advantageous over either of them alone.

Example 15

HEK-293, at a concentration of $1 \times 10^7$ cells/ml, was treated with Mw. Percentage Cell death, employing Trypan blue dye exclusion principle was 80%. Cells pelleted by centrifugation at 1500 rpm for 10 min. Supernatant was discarded. Cell pellets were resuspended in 5 ml of DPBS and total volume was distributed in 5 aliquots of 1 ml each. Cells in each aliquot were counted followed by centrifugation at 1500 rpm for 10 min. Cell pellets were resuspended in 100 μl of 50× Trehalose and incubated at 37° C. for 30 min. 100 μl 10× PVP was added subsequently, and samples again incubated at 37° C. of 30 min. Final volume was made upto 1 ml with DPBS. Total volume was distributed into aliquots of 200 μl each. All aliquots were snap freezed in Liquid Nitrogen and except one freezing control rest all subjected to lyophilisation for approx 48 hrs. Lyophilates reconstituted with 200 μl of DPBS and total no of intact cells counted using haemocytometer. Freezing control yielded 67% intact cells while lyophilisation resulted in 49% intact cell recovery. A combination of the two cryopreservatives appears advantageous over either of them alone.

The addition of PVP to Trehalose leads to a higher recovery of intact cells (~50%) as opposed to either of them alone or addition of Trehalose to PVP.

Example 16

B16F10 cells, at a concentration of 1×10$^7$ cells/ml, were treated with Mw. Percent cell death, determined using trypan blue exclusion assay, was 31%. Total volume was distributed into 10 aliquots of 1 ml each and number of cells in each aliquot was counted before processing. Cells pelleted by centrifugation at 1500 rpm for 10 min. Cell pellets were resuspended in 100 μl of 50× Trehalose and incubated at 37° C. for 15 min. 100 μl 10× HES was then added and samples were again incubated at 37° C. for 15 min. Final volume was made upto 1 ml with DPBS. 200 μl was distributed in glass vials labeled appropriately. Samples were snap freezed in Liquid Nitrogen and except one freezing control rest all subjected to lyophilisation for approx. 48 hrs. Lyophilates reconstituted with 200 μl of DPBS and total number of intact cells counted using hemocytometer. Freezing control yielded 95% intact cells while lyophilisation resulted in 70% intact cell recovery but significant amount of cells were clumped together.

Trehalose+PVP seem to be best among all other tested combinations of different cryopreservatives.

Example 17: Assessment of Cellular Size and Granularity

Figure 1:
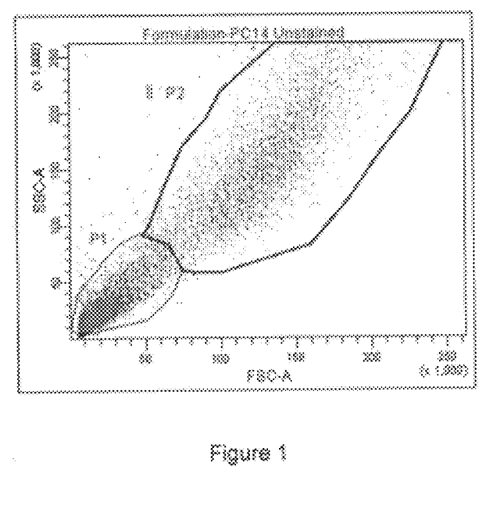
FIG. 1: Determination of Cellular Size and Granularity of lyophilized cells. Forward Scatter measures Cellular Size and Side Scatter measures the amount of granularity.

Flow cytometry can provide information about the cellular size and granularity from homogeneous or heterogeneous tissue/cell suspension in medium. Cellular size is measured as the diffracted laser light generated from the cell membrane; and granularity is the measure of the reflected and refracted light that is emitted upon targeting the granules of a cell. Cellular size is measured on the Forward Scatter (FSC) scale of the dotplot; and granularity on the Side Scatter (SSC) scale of the dotplot. Assessment of the lyophilized cells indicate two distinct population, as shown in FIG. 1. Population P1 appears at a lower FSC and SSC population that population P2, suggesting that population P2 are larger in size and posses more granules compared to population P1.

Example 18: Determination of Cellular Integrity

Figure 2:
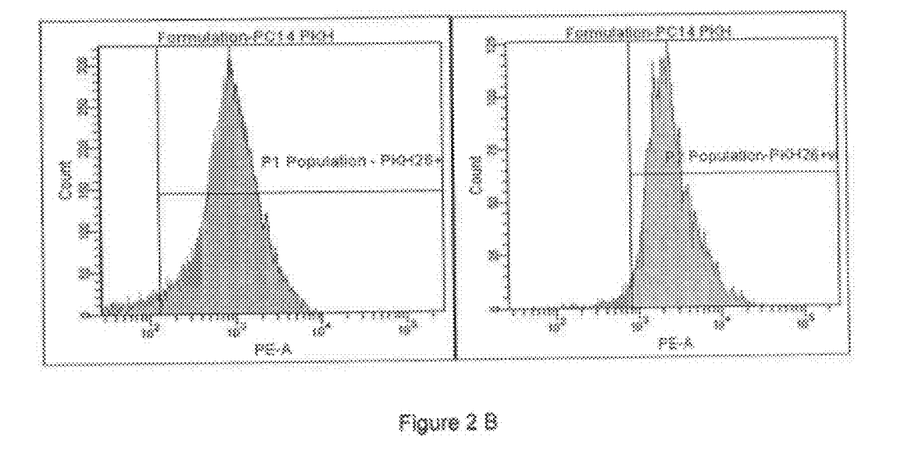
Figure 2A:
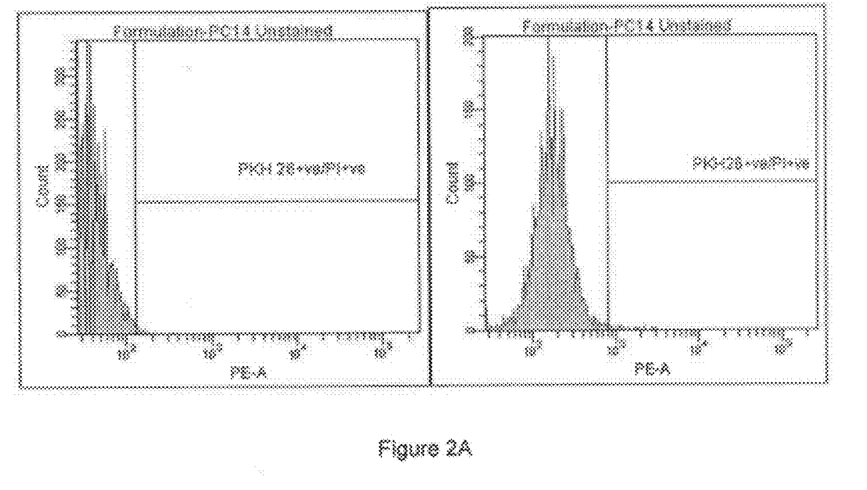

Lyophilized cells were stained with cell membrane lipid binding molecule PKH26. PKH26 is excited by the blue laser and absorbs light at 551 nm and emits light at 567 nm. FIG. 2 shows that both P1 and P2 population uptake the PKH26 dye. Lyophilized cells stained with the PKH26 dye, 90.7% of P1 population and 96.3% of P2 population are PKH26+ve.

Example 19: Determination of Cell Death

Figure 3:
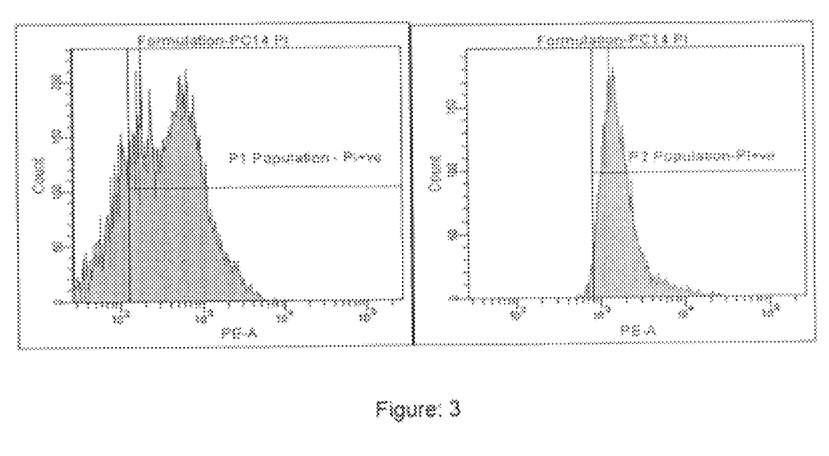
FIG. 3: Lyophilized cells not stained with the PKH26 dye for determining background fluorescence.

Cell death was evaluated by Propodium Iodide (PI) dye, which penetrates into cells with compromised cell membrane. FIG. 3 shows that both P1 and P2 uptake the PI dye, suggesting that both the population are dead. Lyophilized cells stained with PI dye. 78.3% of P1 population and 97.8% of P2 population are PI+ve.

Example 20: Cells with Intact Cell Membrane and Nuclear Envelope

The formulation was stained with Hematoxylin and Eosin to assess cytoplasmic and nuclear membrane integrity. Intact Cells with intact nucleus were observed (FIG. 4).

Example 21

MiaPaCa 2 cells, at a concentration of 1×10$^7$ cells/ml, were treated with Mw. Percentage cell death, determined using trypan blue exclusion assay, and was 100%. Total volume was distributed into 2 aliquots of 5 ml each and number of cells in each aliquot was counted before processing. Cells pelleted by centrifugation at 1500 rpm for 10 min. Cell pellets were resuspended in 100 μl of 50× Trehalose and incubated at 37° C. for 15 min. 100 μl 10× PVP was added subsequently, and aliquots again incubated at 37° C. of 15 min. 200 μl was distributed in glass vials labeled appropriately and were snap freezed in Liquid Nitrogen. One set of vials were lyophilized for approx. 48 hrs. Lyophilates reconstituted with 200 μl of DPBS and cell suspension was injected in Balb/C mice on day 1 and 21. Non-lyophilized formulated cells were administered in control group on day 1 and 21. On day 28, all mice were sacrificed and the splenocytes were isolated. Interferon gamma ELISPOT was performed to assess immune response. The lyophilized cells showed equal number of cells producing interferon gamma indicating retained immunogenicity, infect little better. (FIG. 5).

Example 22

Killed 10$^7$ cells/ml of cancer cells were pelleted by centrifugation at 1500 rpm for 10 min. Supernatant was discarded. Total volume was distributed into aliquots of 1 ml each and cells in each aliquot were counted. Treatment group cell pellet was re-suspended in trehalose at final concentration of 5% w/v (in DPBS) followed by incubation at 37° C. for 15 min. Subsequently PVP was added at final concentration of 1% w/v and cell suspension was incubated at 37° C. for 15 min. Total volume was distributed into aliquots of 1 ml each and cells in each aliquot were counted. Prior to lyophilisation, all aliquots were subjected to snap freezing in Liquid nitrogen. Cells were reconstituted in DPBS.

A Smear was prepared on a glass slide; air dried and fixed using acetone. Blocking for 1 hour with Blocking Buffer containing 5% BSA, Serum, and 2% Triton-X 100 in PBS. Incubated 1 hour with primary antibody targeted against a cell surface marker was used for detection at 1:100 dilutions. Wash with PBS containing triton. Incubated with Anti mouse IgG-FITC labeled Secondary Ab (1:1000). Wash with PBS containing triton.

The surface proteins are detected under florescent microscope as depicted in FIG. 6. The method can be used for the transport of samples tissue killed or live and later use them for diagnosis or forensic.

Both intra-cellular and extra-cellular cyropreservatives are capable of preserving the morphology of Mw treated cells. PVP and trehalose appear advantageous over both dextran and Polysorbate-80 wherein the cells appeared to be clumped.

A combination of the two cryopreservatives appears advantageous over either of them alone. The addition of PVP to Trehalose leads to a higher recovery of intact cells (approx 50%) as opposed to either of them alone or addition of trehalose to PVP.

The method of preservation by lyophilisation can be used for preserving whole cells vaccine candidates with retained immunogenicity, intact structure and nucleic acid. The method can also be used to preserve cell samples for forensic applications and diagnostic purposes.

We claim:

1. A lyophilized composition comprising:
   killed cancer cells, by treating with *Mycobacterium* w (Mw), with substantially retained immunogenicity and morphology:
   trehalose as an intracellular cryo-preservative at 1 to 10% w/v; and,
   polyvinyl pyrrolidone as an extra cellular cryo-preservative at 0.1 to 5% w/v.

2. The composition as claimed in claim 1 further comprising an adjuvant.

3. The composition as claimed in claim 1, wherein the polyvinyl pyrrolidone has a molecular weight ranging from 30 to 50 kilo Daltons.

4. The composition as claimed in claim 2, wherein the adjuvant is selected from the group consisting of oils, aluminium salts, virosomes, dead whole organisms, extracts of microbes and combination thereof.

* * * * *